(12) United States Patent
Wüst et al.

(10) Patent No.: US 10,399,248 B2
(45) Date of Patent: Sep. 3, 2019

(54) SPACER MOULD AND METHOD FOR PRODUCING HIP SPACERS

(71) Applicant: Heraeus Medical GmbH, Wehrheim (DE)

(72) Inventors: Edgar Wüst, Groß-Umstadt (DE); Sebastian Vogt, Erfurt (DE)

(73) Assignee: HERAEUS MEDICAL GMBH, Wehrheim (DE)

(*) Notice: Subject to any disclaimer, the term of this patent is extended or adjusted under 35 U.S.C. 154(b) by 569 days.

(21) Appl. No.: 15/079,096

(22) Filed: Mar. 24, 2016

(65) Prior Publication Data
US 2016/0332328 A1    Nov. 17, 2016

(30) Foreign Application Priority Data
Mar. 27, 2015    (DE) .......................... 10 2015 104 704

(51) Int. Cl.
B28B 7/00    (2006.01)
A61F 2/30    (2006.01)
(Continued)

(52) U.S. Cl.
CPC .......... B28B 7/0097 (2013.01); A61F 2/3094 (2013.01); A61F 2/30942 (2013.01);
(Continued)

(58) Field of Classification Search
CPC .................... B28B 7/14; B28B 7/0097; A61F 2002/30616; A61F 2/3094; A61F 2/30942;
(Continued)

(56) References Cited

U.S. PATENT DOCUMENTS 6,361,731 B1 *   3/2002   Smith ................. A61F 2/30942
                                                     264/271.1
7,789,646 B2     9/2010   Haney et al.
(Continued)

FOREIGN PATENT DOCUMENTS

CN    203619725 U    6/2014
DE    202009012964 U1    3/2010
(Continued)

OTHER PUBLICATIONS

Australian Office Action for corresponding Australian Application No. 2016201669 dated Nov. 7, 2016.
(Continued)

*Primary Examiner* — Philip C Tucker
*Assistant Examiner* — Jimmy R Smith, Jr.
(74) *Attorney, Agent, or Firm* — Norris McLaughlin, P.A.

(57) ABSTRACT

A spacer mold and method for producing a hip spacer, the spacer mold comprises a base element (1), in which a hollow mold is provided as negative image of one side of a femoral stem of the spacer to be generated, whereby a recess connected to the hollow mold is arranged on the proximal end of the hollow mold in the base element. The spacer mold further comprises a semi-spherical insert (2) comprising a femoral head mold as negative image of one side of a femoral head of the spacer to be generated, whereby the semi-spherical insert (2) is to be arranged in the recess in the base element (1). Further, the spacer mold comprises an adapter insert (3) that is designed as a hollow body that is open on two sides and that is or can be arranged in the recess of the base element (1) between the semi-spherical insert (2) and the hollow mold such that the recess exerts a pressure onto the adapter insert (3) and the semi-spherical insert (2). Moreover, the spacer mold comprises a punch (4) that comprises a punch hollow mold in the form of the negative
(Continued)

image of the remaining femoral stem and that is arranged on or can be pressed onto the top side of the base element (1).

13 Claims, 10 Drawing Sheets

(51) Int. Cl.
  *A61F 2/36* (2006.01)
  *B28B 7/14* (2006.01)
  *B28B 3/02* (2006.01)
  *B28B 23/02* (2006.01)
(52) U.S. Cl.
  CPC ............. *A61F 2/36* (2013.01); *A61F 2/3672* (2013.01); *B28B 3/02* (2013.01); *B28B 7/14* (2013.01); *B28B 23/02* (2013.01); *A61F 2002/30616* (2013.01); *A61F 2002/30672* (2013.01); *A61F 2002/30693* (2013.01); *A61F 2002/30957* (2013.01); *A61F 2310/00353* (2013.01)
(58) Field of Classification Search
  CPC . A61F 2/36; A61F 2/3672; A61F 2002/30957
  USPC .................................................. 425/236, 281
  See application file for complete search history.

(56) References Cited

U.S. PATENT DOCUMENTS

| | | | |
|---|---|---|---|
| 8,801,983 B2 | 8/2014 | Haney et al. | |
| 9,033,693 B2 * | 5/2015 | Palazzolo | A21C 11/106 425/118 |
| 2007/0222114 A1 * | 9/2007 | Ziran | A61F 2/30942 264/279 |
| 2009/0146342 A1 * | 6/2009 | Haney | A61F 2/30942 264/250 |

FOREIGN PATENT DOCUMENTS

| | | |
|---|---|---|
| EP | 2522310 A1 | 11/2012 |
| EP | 2787928 A1 | 10/2014 |
| WO | 2009/073781 A2 | 6/2009 |
| WO | 2013/086177 A1 | 6/2013 |

OTHER PUBLICATIONS

European Searh Report Action for corresponding European Application No. 16158937.9 dated Sep. 1, 2016.
Kuehn, Klaus-Dieter; "Knochenzemente fuer die Endoprothetik"; Springer-Verlag, 2000, pp. 18-19, Springer-Verlag of BertelmannSpringer publishing group, Berlin, Germany.

\* cited by examiner

SPACER MOULD AND METHOD FOR PRODUCING HIP SPACERS

The invention relates to a spacer mould for producing a temporary hip spacer for a two-stage revision surgery. The invention also relates to a method for producing a hip spacer of this type and to hip spacers produced with a method of this type and/or to a spacer mould of this type.

Cemented and non-cemented total articular endoprostheses (TEPs) are currently the state of the art in orthopaedics. Unfortunately, TEPs are associated with a small number of early and late infections, approx. 2-6%. Infected TEPs usually necessitate a revision surgery. Said revision surgeries can be subdivided into one-stage and two-stage operations. Two-stage revision surgery involves removing the infected TEP first, followed by debridement of the infected bone and soft tissue, and subsequently inserting a spacer as temporary placeholder. In this context, it is customary to use industrially pre-made spacers that may contain an antibiotic or to use tailor-made spacers made of polymethylmethacrylat bone cement (PMMA bone cement) which are either shaped freely or through the use of casting moulds by the surgeon. Said spacers can be fabricated in patient-specific manner through tailor-made doping of the PMMA bone cement used in them with antibiotics in accordance with the antibiotic profile of the pathogens underlying the infection.

The currently available industrially-prefabricated spacers are available in various sizes and geometries that match the majority of the possible anatomical scenarios more or less well. Said prefabricated spacers for hip joints (hip spacer) contain a steel core to provide the hip spacer with sufficient mechanical stability.

Spacers can be freely shaped by the surgeon or through the use of casting moulds. These casting moulds have filling openings through which the PMMA cement dough is usually pressed by means of a cementing system and through the use of manually-driven dispensing devices. The casting moulds therefore need to resist the injection pressure without the casting moulds being driven apart or changing shape. Therefore, suitable closures for fixation of the casting moulds are required.

Spacers usually stay in place in the patient for a period of several weeks, often for 6 to 8 weeks, until the infection subsides. Subsequently, the spacer is removed in a second surgery, the surrounding tissue is again subjected to debridement, and then the revision prosthesis of a cemented or non-cemented type is inserted.

A simple two-part casting mould made of translucent plastics for hip spacers is disclosed in the patent, U.S. Pat. No. 6,361,731 B1. This device comprises a port as filling opening into which the PMMA bone cement dough is injected by means of a dispensing tube of a cementing system. This casting mould can be filled only with a PMMA bone cement dough that has a low viscosity at room temperature. For this purpose, either a low viscosity PMMA bone cement is used or a PMMA bone cement with a high viscosity at room temperature, whose cement components have been pre-cooled immediately after being mixed such as to have a lower viscosity for several minutes such that it can be poured similar to the PMMA bone cement that has a low viscosity at room temperature.

US 2007/0 222 114 A1 describes a hip spacer mould. Said spatial mould consists of a multitude of old segments that are being connected to each other. Due to the multitude of segments, the spacer mould can be adapted relatively well to the anatomical situation of the patient. The spacer mould segments are joined to each other by means of screw clamps. The PMMA bone cement dough is introduced through channels in the spacer mould. Due to the complex design of the casting mould, joining the spacer mould segments and removing the hip spacer once the PMMA bone cement dough is cured is very laborious.

WO 2009/073 781 A2 proposes a spacer mould for a hip spacer consisting of two parts that can be shifted with respect to each other in order to be able to adapt the length of the hip stem. The part forming the hip stem consists of two mirror-symmetrical semi-shells that can be taken apart. The PMMA bone cement dough is introduced through a feed opening into the hollow space. The individual parts of the mould are connected to each other by means of screw connections. All screws need to be loosened to allow the spacer to be removed. Accordingly, the intraoperative production is relatively time-consuming and bears the risk of an elevated infection rate. The small parts make for difficult handling in the often hectic surgical routine.

EP 2 522 310 A1 discloses another casting mould. Said device consists of at least two parts, whereby an insertion section is arranged in a first part and an insertion receptacle is arranged in the second part. Both parts can be plugged into each other and form a casting mould for the production of the stem of a hip spacer.

EP 2 787 928 A1 describes a complex casting mould. Said casting mould facilitates the production of hip spacers with different spherical heads. The elements of the casting mould are fixed to each other by means of connecting elements.

Casting moulds resembling the one from EP 2 787 928 A1 have been described in the U.S. Pat. No. 7,789,646 B2 patent and in the U.S. Pat. No. 8,801,983 B1 patent.

The known spacer moulds and methods for producing hip spacers are disadvantageous in that the spacer mould, as a casting mould, needs to be filled with bone cement in a laborious procedure and at high pressure. Either a relatively low viscosity bone cement needs to be fed through filling openings or a flexible spacer mould must expand while it takes up the bone cement. Due to the forces arising in this process, the parts of said spacer moulds usually need to be connected and stabilised with respect to each other in laborious manner. The parts required for this purpose are complex and therefore expensive to build up and/or consist of multiple parts, which makes their assembly disadvantageous in the often hectic surgical routine.

Accordingly, it is the object of the invention to overcome the disadvantages of the prior art. Specifically, the device to be developed shall allow the medical staff to produce, under surgery conditions, a spacer with antibiotic-doped PMMA bone cement dough, whose shape comes close to the individual anatomical situation of the patient.

The design of the spacer mould to be developed shall be appropriate such that the production of hip spacers with PMMA bone cement through the use of vacuum mixing systems and also without the use of these mixing systems, for example through the use of simple mixing cups and spatulas, is made feasible. It shall be feasible to use the spacer mould to be developed to produce hip spacers with PMMA bone cements that have a high viscosity and with PMMA bone cements that have a low viscosity at room temperature. The design of the device shall largely exclude the formation of sharp burrs on the spacer, since these have to be removed mechanically in laborious manner prior to the implantation. It shall be feasible to fill the device with PMMA bone cement dough without applying high pressures offer level that is produced during the filling process by the vacuum mixing systems in the previously known devices. By this means, and in general, there should, to the extent possible, be no separate closing elements required, such as clips or screws. Moreover, the spacer mould should, to the extent possible, not contain any separate, sharp-edged locking elements for fixation of elements of the device. For hygienic reasons, the spacer mould should be suitable as a disposable product for single use and therefore its production should be as inexpensive as possible.

The objects of the invention are met by a spacer mould for producing a hip spacer, whereby the spacer mould comprises the following parts:
A) a base element, in which a hollow mould is provided as negative image of one side of a femoral stem of the spacer to be generated, whereby a recess connected to the hollow mould is arranged on the proximal end of the hollow mould in the base element;
B) a semi-spherical insert comprising a femoral head mould as negative image of one side of a femoral head of the spacer to be generated, whereby the semi-spherical insert is or can be arranged in the recess in the base element at a side of the recess that is opposite to the connection to the hollow mould, such that the femoral head mould is aligned in the direction towards the hollow mould;
C) an adapter insert that is designed as a hollow body that is open on two sides and that is or can be arranged in the recess of the base element between the semi-spherical insert and the hollow mould such that the recess exerts a pressure onto the adapter insert and the semi-spherical insert when the adapter insert and the semi-spherical insert are inserted into the recess, whereby the hollow body of the adapter insert connects the femoral head mould of the semi-spherical insert to the hollow mould in the base element; and
D) a punch that comprises a punch hollow mould in the form of the negative image of the remaining femoral stem and that is arranged on or can be pressed onto the top side of the base element;
whereby a cutting edge bounding the connection of the hollow mould of the base element to the punch hollow mould of the punch is arranged on the edge of the hollow mould of the base element and/or on the edge of the punch hollow mould of the punch, and a cutting edge bounding the connection of the femoral head mould to the opening of the hollow body of the adapter insert is arranged on the edge of the femoral head mould and/or on the edge of said opening of the hollow body of the adapter insert to the femoral head mould.

A spacer mould according to the invention must be well-suited for producing a hip spacer (only called spacer, in some places, hereinafter) having a head and a femoral stem. For this purpose, the spacer mould assembled as intended must form a negative image of the head of the hip spacer and a negative image of the femoral stem of the hip spacer. The two negative images (of the head and of the stem) must be connected to each other, i.e. jointly form a mould as the negative image of the hip spacer. For this purpose, the head mould and the femoral stem mould are connected to each other through a neck mould that forms a negative image of the neck of the hip spacer to be generated.

A semi-spherical insert shall be understood to be a not strictly geometrically shaped semi sphere as femoral head mould. The semi-spherical insert can be a negative image of a spherical segment or of a segment of a coarsely spherical shape that is well-suited for forming the head of the hip spacer.

The proximal end of a femoral stem is the end at which the head of the femur is connected to the femoral stem by means of the neck. The head of the femur comprising an approximately spherical articular surface forms a connection (sliding surface) with the pelvic bones, and therefore forms the hip joint. Presently, the same anatomical terms are used for the hip spacer and for the spacer mould, which in fact is a negative image of the hip spacer to be generated. Obviously, the femoral stem is kept shorter in the hip spacer than in a real femur, since not all of the femur is to be replaced, but mainly the head along with its sliding surface. Moreover, the femoral stem of the hip spacer is usually designed to be narrower and/or slimmer in order to be able to anchor the hip spacer by means of the femoral stem in the femur (or in the stem of the femur, as may be the case) of the patient.

The side of the femoral stem, which is replicated by the hollow mould of the base element and by the punch hollow mould of the punch, as negative image, is aligned in axial direction of the stem. The axial direction of the stem, or of the replicated part of the femur, as the case may be, is preferably aligned parallel to the open top side of the hollow mould, particularly preferably the axis of the femoral stem is situated in the open plane of the hollow mould. The open top side of the hollow mould is bounded by the edge. Alternatively, the axial direction can also be at an angle of maximally 30° with respect to the open plane of the open hollow mould, preferably it can be at an angle of maximally 10° with respect to the open plane of the open hollow mould. The same applies accordingly to the punch hollow mould.

The remaining femoral stem and/or the negative image of the remaining femoral stem in the scope of the present invention is the surface of the negative image of the femoral stem of the hip spacer generated that is replicated neither by the hollow mould of the base element nor by the inside of the hollow body of the adapter insert. Accordingly, the punch hollow mould of the punch generates the remaining surface of the femoral stem and/or of the hip spacer by pushing the punch onto the remaining assembled mould parts (hollow mould, femoral head mould and hollow body) filled with an excess of PMMA bone cement.

If reference is made to cutting edges (plural) in the scope of the present invention, this shall also encompass a circumferential one-part cutting edge that could be considered to be a single cutting edge. A cutting edge has an angle, in cross-section, (also called wedge angle) of less than 90°, preferably of maximally 45°. A cutting-edge can also be called blade. The cutting edges can be arranged just on one side or on both sides of the mould parts to be connected. Preferably, just the connection of the punch to the adapter insert has no cutting edge provided in it, since no cutting can proceed during punching in the direction of the base element.

Moreover, the invention can provide the base element, next to the recess, to slope towards the outside with respect to the recess.

According to the invention, it is preferred to appropriately apply the punch to the base element such that no through-going gap remains between the base element and the punch, in particular such that no through-going gap remains between the edge of the hollow mould of the base element and the punch. Preferably, the hollow mould, the femoral head mould, the punch hollow mould and the hollow body can be placed against each other and/or connected to each other such that a closed inner mould for the hip spacer is formed, whereby ventilation openings may be provided for ventilation of the inner mould (of the spacer mould).

The present invention also proposes the femoral head mould to comprise a circumferential edge and the surface contour of the circumferential edge of the femoral head mould of the semi-spherical insert to be sloping towards the outside originating from the femoral head mould.

In this context, sloping towards the outside is meant with respect to the plane of the edge of the femoral head mould. By this means, it can be ensured that cut-off PMMA bone cement residues can be removed and/or drop away from the femoral head mould into the widening gap between the semi-spherical insert and the adapter insert.

Moreover, the invention can provide the cutting edges to bound the entire hollow mould in the base element and/or the cutting edges to bound the entire femoral head mould in the semi-spherical insert and/or the entire hollow body of the adapter insert, in the connection to the femoral head mould, to be bounded by a cutting edge.

This ensures that the hip spacer to be generated is fully deburred by the cutting edges. The invention can just as well provide the cutting edges to bound the entire hollow mould in the base element except in the connection to the recess.

A particularly preferred refinement of the present invention can provide the base element, next to the hollow mould, to slope towards the outside with respect to an edge of the hollow mould.

The base element, next to the hollow mould, sloping towards the outside with respect to an edge of the hollow mould means that, if the base element has a planar bottom side, for example for setting up the base element on a planar surface such as a table, then the thickness of the base element decreases towards the outside perpendicular to the planar bottom side originating from the edge of the hollow mould. In this context, the hollow mould is arranged on the top side of the base element that is opposite to said bottom side. In this context, there is no edge of the hollow mould in the connection of the hollow mould to the recess, i.e. the hollow mould comprises no edge in the scope of the present invention at the connection to the recess. However, cutting edges can be arranged at the connection of the hollow mould to the recess for severing excess PMMA bone cement that exits from the spacer mould in the connection of the hollow mould of the base element to the hollow body of the adapter insert. If the base element has no planar bottom side, for example because the base element has a different set-up option, a plane parallel to the edge of the hollow mould can still be defined such that the distance of the top side of the base element and said imagined plane (for example parallel to the bottom of the set-up site or to a table top) decreases towards the outside originating from the edge of the hollow mould. The angle of inclination at the edge of the hollow mould preferably is 1° to 60°, particularly preferably 1° to 20°. This consideration may be done analogously for the edge of the femoral head mould and the same angles of inclination may be provided.

Due to the inclination, severed PMMA bone cement can drop off outwards and/or can slip away outwards. This prevents the cured PMMA bone cement from connecting the parts of the spacer mould to each other.

Spacer moulds according to the invention can also be characterised in that the base element comprises, on the bottom side, a planar support surface or a pedestal for set-up of the spacer mould on a planar support.

This simplifies the operation of the spacer mould. The spacer mould can simply be set-up on a table for inserting the semi-spherical insert and the adapter insert and for filling the hollow mould from above with PMMA bone cement. Presently, the terms, top and bottom, are always used as a way of reference to said kind of set-up of the base element.

Moreover, the invention can provide the adapter insert to be a two-part or multi-part adapter insert, whereby the parts of the adapter insert can be attached to each other or placed against each other, whereby, preferably, cutting edges are provided on the parts of the adapter insert, whereby the cutting edges are arranged on the edges of the moulds forming the hollow body that form the connections of the hollow body in the adapter insert.

As a result, the adapter insert can be filled with PMMA bone cement more easily, which simplifies the applicability of the spacer mould. Preferably, the parts of the adapter insert can be or are connected to each other in a form-fit manner.

To obtain a particularly inexpensive design for single use, the invention can provide the base element, the semi-spherical insert, the adapter insert and the punch to be fabricated from plastic material.

The use of plastic material is made possible only through the design according to the invention. As a result, the spacer mould can be supplied as an inexpensive disposable product. Reusability should best be excluded during the production of the spacer due to the requisite hygiene.

According to the invention, it is preferred to provide the recess of the base element to have a smaller circumference than the circumference of the semi-spherical insert with the adapter insert touching against it.

As a result, the semi-spherical insert and the adapter insert are pressed together when they are inserted into the recess of the base element while touching against each other. By this means, it can be ensured that the cutting edge connecting the femoral head mould to the hollow body severs excessive PMMA bone cement. Moreover, this also ensures that the mechanical strain to which the semi-spherical insert and the adapter insert are exposed when a core for stabilisation of the hip spacer is pressed into the PMMA bone cement present in the femoral head mould and the hollow body can be absorbed without deformation and without the two inserts coming apart.

To prevent burrs or uneven sites from being present on the sliding surface, the invention can provide the semi-spherical insert to be designed as a single part.

As a result, interfering burrs on the sliding surface of the femoral head of the spacer can be prevented. Otherwise, said burrs would have to be removed in laborious manner since they can lead to inflammation and/or complications during the healing process if fragments of them become detached.

Moreover, the invention can provide the width of the semi-spherical insert surrounding the edge of the femoral head mould to be between 5 mm and 45 mm wide.

As a result, various semi-spherical inserts can be used to form differently-sized femoral heads. As a result, the space of mould becomes adaptable to different anatomical scenarios.

A refinement of the invention proposes to provide ventilation openings, in particular ventilation bore holes, in the punch, preferably to provide through-going ventilation openings in the punch hollow mould.

Having the ventilation openings and/or the ventilation pore calls allows enclosed air that possibly remains in the spacer mould to escape. The tips on the spacer thus generated may need to be removed from the spacer mould after the hip spacer is taken out Spacer moulds according to the invention can be characterised in that the spacer mould comprises no filling opening for filling PMMA bone cement into them.

As a result, the laborious filling of the space of form with bone cement can be avoided. The advantage of the spacer mould according to the invention specifically is that no laborious filling through a filling opening of this type is required. Due to the moulds of the base element, of the semi-spherical insert and of the adapter insert being openly accessible, the spacer mould according to the invention can be filled easily and even by laymen.

To attain higher variability of the spacer mould, the invention can provide the spacer mould to comprise at least one insert for the hollow mould and/or the punch hollow mould that is or can be inserted into the hollow mould and/or the punch hollow mould such that the size and/or the shape of the femoral stem of the hip spacer to be generated can be varied by means of the insert.

As a result, various femoral stems can be generated with the spacer mould. The invention can just as well provide to have various semi-spherical inserts and adapter inserts with differently-shaped femoral head moulds and hollow bodies to be present by means of which different necks and femoral heads of the hip spacer can be produced. Preferably, the adapter inserts can be combined with matching semi-spherical inserts. In particular, the semi-spherical inserts differ by femoral head moulds with different diameters.

The objects underlying the invention are also solved through a method for producing a hip spacer comprising the steps of:

A) filling a femoral head mould of a semi-spherical insert and a hollow body, open on two sides, of an adapter insert with PMMA bone cement and assembling the semi-spherical insert and the adapter insert;
B) followed by plugging the assembled and PMMA bone cement-filled semi-spherical insert and adapter insert into a recess of a base element, whereby an excess of PMMA bone cement is severed by cutting edges at the connection between the femoral head mould and the hollow body, whereby the base element comprises a hollow mould as negative image of a part of the femoral stem of the hip spacer to be generated, whereby the hollow mould, after being plugged in, is situated adjacent to the remaining free opening of the hollow body of the adapter insert;
C) followed by plugging a head of a core for mechanical stabilisation of the hip spacer into the PMMA bone cement present in the hollow body of the adapter insert connected to the semi-spherical insert, such that a fin of the core is arranged in the hollow mould of the base element;
D) filling the hollow mould of the base element with an excess of PMMA bone cement;
E) followed by pushing a punch with a punch hollow mould as negative image of the remaining part of the femoral stem of the hip spacer to be generated onto the PMMA bone cement in the hollow mould, such that the femoral head mould, the hollow body of the adapter insert, the hollow mould of the base element, and the punch hollow mould of the punch define the shape of the hip spacer to be generated, whereby an excess of PMMA bone cement is severed by cutting edges at the connection between the hollow mould of the base element and the punch hollow mould while the punch is being applied; and
F) followed by taking the finished hip spacer out of the spacer mould after the PMMA bone cement has cured in the spacer mould formed by the base element, the semi-spherical insert, the adapter insert, and the punch.

It is feasible to first fill the femoral head mould of the semi-spherical insert and, if applicable, also the hollow body of the adapter insert with PMMA bone cement and to then assemble the semi-spherical insert and the adapter insert, and it is also feasible to first assemble the semi-spherical insert and the adapter insert and to then, subsequently, fill the femoral head mould of the semi-spherical insert and the hollow body of the adapter insert with PMMA bone cement. Moreover, it is feasible to first fill the femoral head mould with PMMA bone cement, followed by adding the adapter insert, and subsequently filling the yet unoccupied volumes with PMMA bone cement dough through the free opening of the hollow body (preferably with an excess thereof).

The fin is connected to the head of the core and preferably is provided as a single part.

Preferably, the femoral head mould of the semi-spherical insert and the hollow body of the adapter insert are filled with an excess of PMMA bone cement. By this means, it can be ensured that no hollow spaces containing no PMMA bone cement remain in the hollow body and in the femoral head mould. By this means, hollow spaces and recesses in the surface of the hip spacer are prevented.

The spacer mould is formed by the base element, the semi-spherical insert, the adapter insert, and the punch, or, to be more exact, by the hollow mould of the base element, the femoral head mould of the semi-spherical insert, the hollow body of the adapter insert, and the punch hollow mould of the punch.

Methods according to the invention can just as well provide a metal core, in particular a steel core, to be used as core for mechanical stabilisation of the hip spacer.

These materials possess high stability. Cores (also called reinforcements) for stabilisation of hip spacers are known.

In methods according to the invention, it is particularly preferable to provide the method to be carried out while using a spacer mould according to the invention.

Moreover, the invention can provide distance pieces to be arranged on the core, whereby at least one of the distance pieces touches against the hollow mould of the base element after the head of the core has been plugged into the hollow body of the adapter insert connected to the semi-spherical insert.

The distance pieces are preferred to consist of PMMA. The distance pieces are also preferred to extend star-shaped radially away from the core. As a result, the core is being arranged in the spacer mould in the correct position and orientation.

And lastly, methods according to the invention also propose the adapter insert to be pressed against the semi-spherical insert by the circumferential base element after the adapter insert and the semi-spherical insert are plugged into the recess of the base element, whereby the adapter insert preferably is pressed against the cutting edge of the semi-spherical insert.

The semi-spherical insert and the adapter insert are fixed to each other by this means such that they do not detach from each other or move with respect to each other when exposed to a mechanical strain, such as during the insertion of the core. Moreover, deburring of the hip spacer to be generated is attained by means of the cutting edges.

The objects underlying the present invention are also met by a hip spacer produced through a method of this type and/or produced with a spacer mould of this type.

The invention is based on finding, surprisingly, that the simple design and the use of a punch allow the spacer mould to be filled easily with PMMA bone cement through large openings (the open hollow mould, the open femoral head mould, and the opened hollow body) without the PMMA bone cement having to be pressed into the spacer mould at high pressure. By this means, even high viscosity PMMA bone cements can be used for producing the hip spacer. Receiving the semi-spherical insert and the adapter insert in a recess of the base element is an easy means for attaining a stabilisation of these parts with respect to each other. The use of cutting edges allows a largely burr-free surface of the hip spacer to be generated.

The underlying rationale of the invention is to combine the advantages of casting devices, such as high dimensional stability for rounded moulds, with the advantages of embossing devices, such as the severing of burrs and easy shaping in the case of flat moulds. This is attained through the use of a punch as embossing device.

The base element affixes the semi-spherical insert and the adapter insert and pushes them against each other. This is important also for the insertion of the core and/or of the metal core to make sure that the inserts (semi-spherical insert and adapter insert) are not driven apart or deformed when the metal core is being inserted. In this context, the design according to the invention requires no clamps, clips or other fastening means as closure elements, which would only hamper the surgical routine.

The production of the hip spacer can proceed such that, for example, initially the "semi-sphere" of the femoral head mould of the semi-spherical insert is filled with PMMA bone cement and then the two-part adapter insert (in the form of the further "semi-sphere parts") is inserted and then filled completely with PMMA bone cement. Preferably, the adapter insert is filled first and is then connected to the semi-spherical insert. The punching step follows last. The punching can also be called embossing step.

The spacer mould according to the invention has a modular design. It does not need to be filled under pressure, such that no deformation of the spacer mould occurs, and there also is no need for the design of the spacer mould to be pressure-resistant.

A highly viscous PMMA bone cement shall be understood to be those PMMA bone cements that have but a short swelling phase and rapid absence of tackiness (within less than 1.5 minutes). The viscosity remains constant for a long period of time during the processing window and increases only towards the end of that phase. Usually, the processing window is relatively large. The curing proceeds 1.5 to 2 minutes after the end of the processing phase. In this context, referred to Klaus-Dieter Kühn, "Knochenzemente für die Endoprothetik", Springer-Verlag 2001 (ISBN 3-540-41182-8), specifically pages 18 and 19. Cements and/or cement dough shall also be considered to be highly viscous if they remain tack-free for 60 to 90 seconds.

The viscosity itself is not well-suited for a definition since it keeps changing while the bone cement is cured.

Usable highly viscous bone cements include, for example, Palacos® R+G, Palacos® R made by Heraeus Medical GmbH, SmartSet® GHV made by DePuy Orthopadie GmbH, "Bone Cement" made by Biomet Deutschland GmbH.

A spacer mould according to the invention for producing hip spacers can be assembled, for example, from
a) a base element containing a hollow mould in the form of a half of a femoral stem, whereby a recess connected to the hollow mould is arranged at the proximal end of the hollow mould, and whereby a cutting edge that extends around the entire hollow mould of the femoral stem is arranged at the edge of the hollow mould, and whereby the base element, next to the cutting edge, drops off outwards with respect to a plane parallel to the longitudinal axis of the hollow mould;
b) a semi-spherical insert that is arranged or is to be arranged in the recess and is provided in the form of a semi-spherical mould (as femoral head mould) with a circumferential edge, whereby the semi-spherical surface of the semi-spherical mould is arranged or is to be arranged opposite with respect to the hollow mould, whereby a circumferential cutting edge is arranged at the edge of the semi-spherical mould, and the surface contour of the circumferential edge drops off outwards originating from the cutting edge;
c) an adapter insert that is provided as hollow body and is arranged or is to be arranged in the recess between the semi-spherical insert and the hollow mould, whereby the adapter insert connects the semi-spherical mould to the hollow mould; and
d) a punch that comprises a punch hollow mould in the form of a half of a femoral stem that is arranged or is to be arranged on the top side of the base element.

For reinforcement, a steel core is inserted into the spacer mould according to the invention. Said steel core is kept at a distance from the internal contour of the spacer mould, in particular of the hollow mould of the base element and the punch hollow mould of the punch, by star-shaped distance pieces to allow the PMMA bone cement dough to fully envelope the steel core. The distance pieces are preferably formed from PMMA or also from PMMA bone cement.

The device according to the invention contains no separate closing devices or closure devices, such as clips or screws.

The device possesses no special filling opening for PMMA bone cement dough.

The invention can provide the base element, the semi-spherical insert, the adapter insert and the punch to be fabricated from plastic material.

The recess of the base element preferably has a smaller circumference than the circumference of the semi-spherical insert with the adapter insert touching against it. As a result, after insertion of the semi-spherical insert and the adapter insert into the recess of the base element, a tension is generated by means of which the semi-spherical insert and the adapter insert are pressed against each other. By this means, the cutting edge at the semi-spherical insert severs the excess of PMMA bone cement dough from the PMMA bone cement dough in the mould cavity formed by the semi-spherical insert and the adapter insert and pushes the excess of PMMA bone cement into the hollow space formed by the surface contour of the semi-spherical insert and the adapter insert that drops off outwards. This prevents the formation of burrs on the head of the hip spacer.

The semi-spherical insert is preferably provided as a single part. As a result, there is no separation site on the sliding surface of the sphere and/or on the head of the hip spacer, which are strained tribologically after the implantation. Separation sites on tribologically strained sliding surfaces of spacers can lead to increased abrasion. Abraded particles of spacers can cause inflammatory processes.

It is advantageous to have the edge of the semi-spherical insert be between 5 mm and 45 mm wide. As a result, it is feasible to produce semi-spherical moulds with different semi-sphere diameters. When the diameters of the semi-sphere are larger, the edge and/or the width of the edge is simply reduced and the outer dimensions of the semi-spherical insert remain constant. As a result, it is feasible to insert semi-spherical inserts with different semi-sphere diameters into the recess of the base element without having to change the shape and size of the recess of the base element. The diameter of the mould cavity of the semi-spherical element can vary from 46 mm to 75 mm. By this means, the spacer mould according to the invention can be used to produce hip spacers with a sphere diameter of 46 mm up to 75 mm.

Moreover, the offset of the hip spacer can be varied, as a matter of principle, through a combination of adapter inserts with different lengths of the circumferential edge and through the use of semi-spherical inserts with different widths of the circumferential edge.

Moreover, the invention can further provide the adapter insert to be provided as two parts, whereby the two mould parts of the adapter insert are connected to each other in a form-fitting manner.

Moreover, it is advantageous for the punch to possess ventilation bore holes at its top side.

The spacer mould according to the invention is advantageous in that these can be filled without the application of pressure. Large accesses to the mould cavities are present such that the spatial mould can be filled both by hand by means of a spatula or by means of cementing cartridges. In this context, it is particularly advantageous that PMMA cement dough can be used that is highly viscous at room temperature of the type that is used most commonly during knee and hip TEP implantations. This eliminates the need for pre-cooling of highly viscous PMMA bone cement, as is required with the conventional casting moulds, in order to keep the PMMA bone cement sufficiently viscous for a sufficiently long time. In contrast to the known casting devices, the device according to the invention has no feeling opening through which the PMMA bone cement dough would need to be pressed, whereby the cement dough must be pressed through the entire casting device and replaces the air that is present therein. Moreover, it is advantageous that an excess of PMMA cement dough is cut off from the cement dough in the mould cavities by means of the cutting edges. By this means, the formation of burrs is minimised and/or prevented. It is another advantage of the device that the handling of the device is very simple.

The scope of the invention also includes, for example, a method for producing spacers, in which
a) the semi-spherical insert is being filled completely with PMMA bone cement dough;
b) the adapter insert is being filled completely with PMMA bone cement dough;
c) then the cement dough-filled semi-spherical insert and the PMMA bone cement dough-filled adapter insert are being pressed together and plugged into the recess, whereby the cutting edge of the semi-spherical insert is pressed against the wall of the adapter insert and excess PMMA bone cement dough is being severed from the PMMA bone cement dough-filled internal space of the semi-spherical insert and of the adapter insert, and is being pushed into the hollow space between the semi-spherical insert and the adapter insert;
d) the head of the steel core is being plugged into the PMMA bone cement dough that is arranged in the semi-spherical insert and the adapter insert, whereby the steel core rests on the surface of the hollow mould by means of the distance pieces;
e) the hollow mould of the base element is being filled with PMMA bone cement dough until it is completely filled and the PMMA bone cement dough protrudes upwards beyond the edge of the base element;
f) the punch is being pushed onto the PMMA bone cement dough-filled hollow mould of the base element, whereby the punch is being pressed against the cutting edge of the base element and the excess PMMA bone cement dough is being severed from the cement dough in the hollow mould and is being pushed into the space between the base element, which drops of outwards, and the punch; and in which
g) the hip spacer is taken out of the spacer mould after the PMMA bone cement dough is cured.

The method according to the invention is a combination of a casting method and an embossing method and/or punching method. The method is advantageous in that the PMMA bone cement can be filled into the spacer mould both by hand using a spatula and with a cementing system without involving the use of pressure. By this means, it is feasible to even use highly viscous PMMA bone cements at room temperature without pre-cooling. Moreover, it is advantageous that the pressure-less filling of the device prevents the spacer mould from being driven apart, as can occur with the previously known casting moulds. By this means, there is no need for resource-consuming separate closing devices, such as clips and screws. Process step (g) represents an embossing of half of the stem contour. One advantage of the embossing step is that enclosed air is pushed out of the mould towards the side, past the punch.

BRIEF DESCRIPTION OF THE DRAWINGS

Exemplary embodiments of the invention shall be illustrated in the following on the basis of ten schematic figures, though without limiting the scope of the invention. In the figures:

FIG. 6: shows a schematic perspective view of the base element according to FIG. 3, in which the semi-spherical insert according to FIG. 5 and a lower half of an adapter insert according to FIG. 8 are inserted and a steel core according to FIG. 4 is placed in;

DETAILED DESCRIPTION OF THE DISCLOSURE

Figure 1:
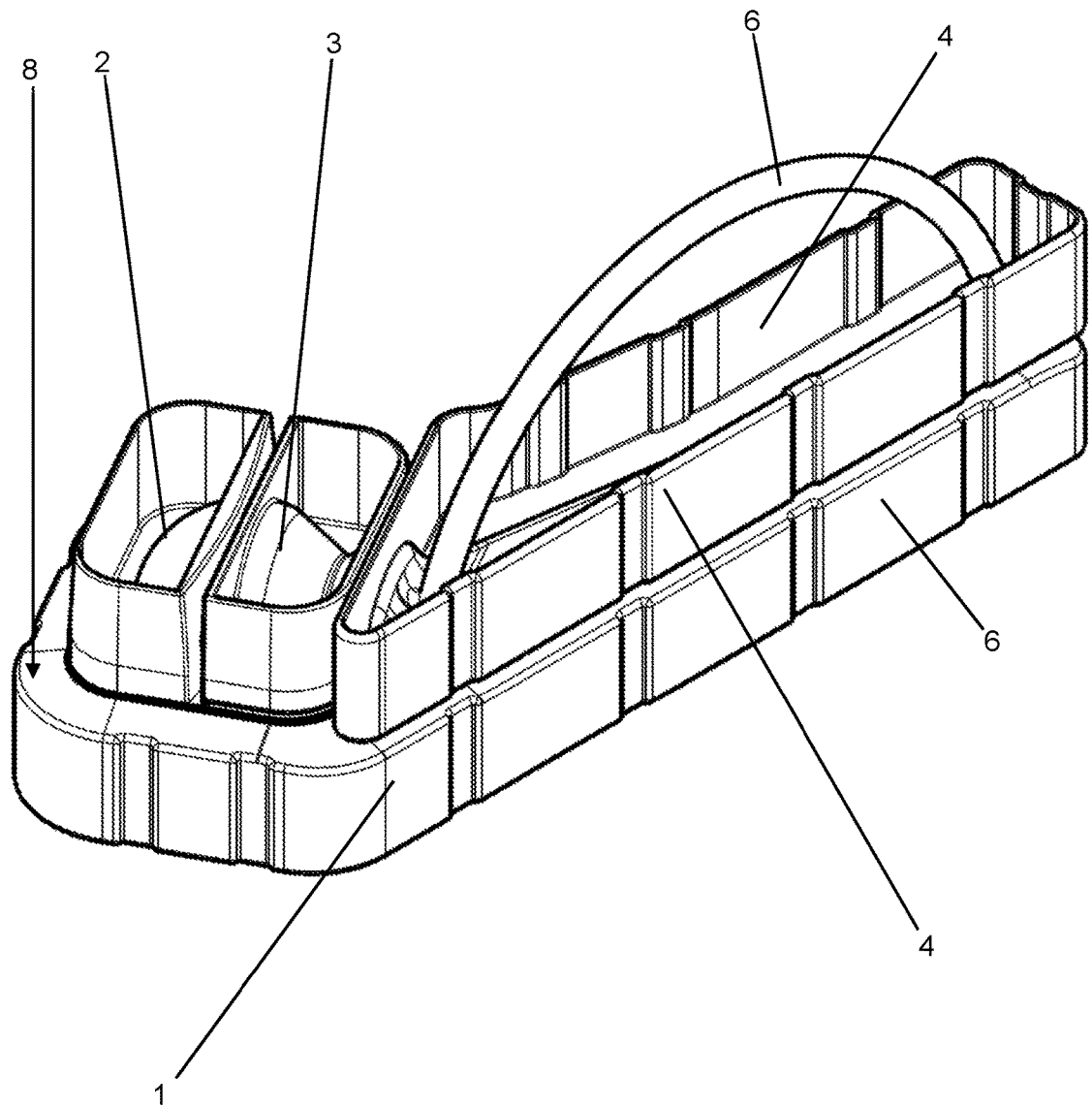
FIG. 1: shows a schematic perspective view of the top side of a spacer mould according to the invention.
Figure 2:
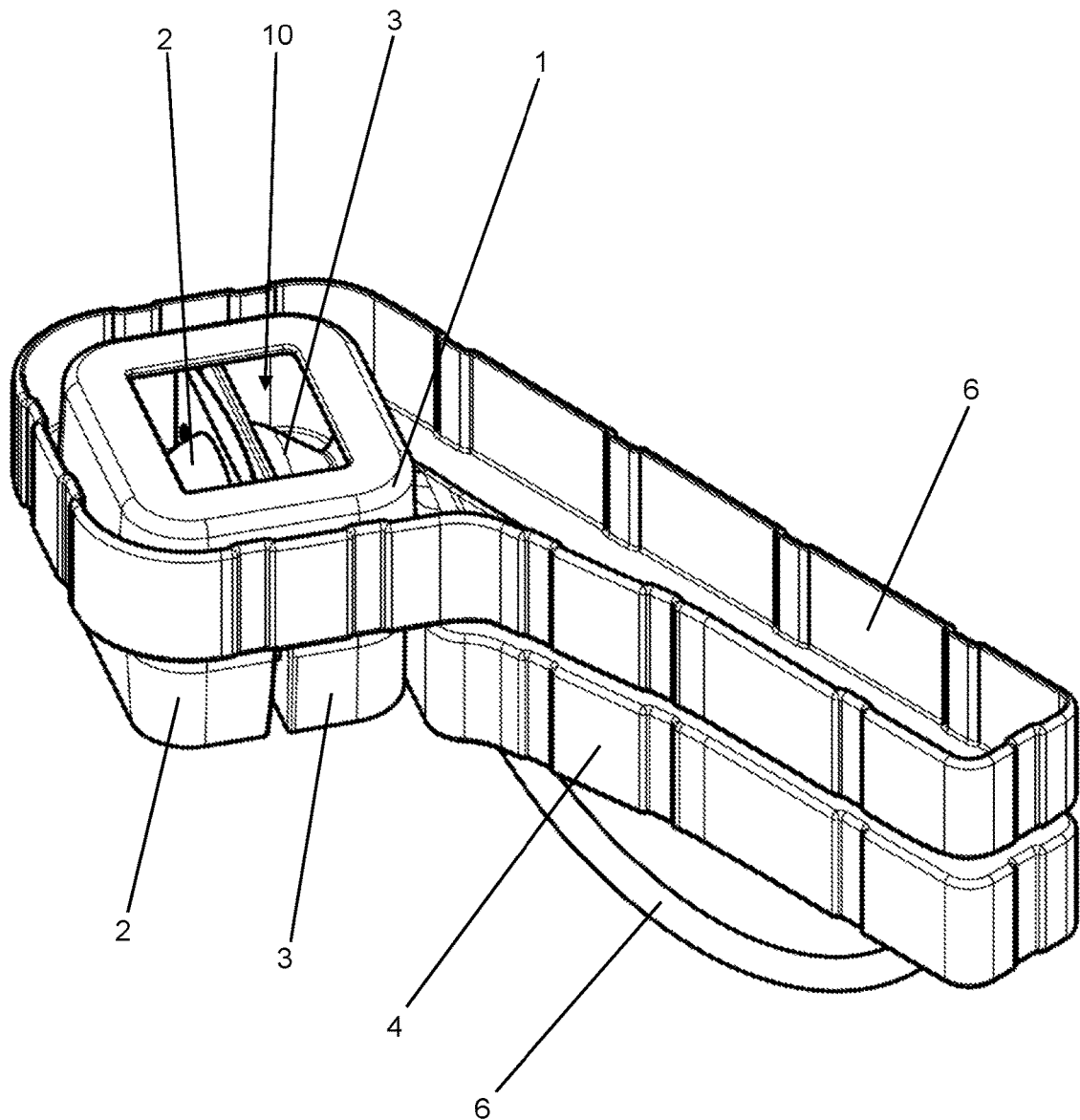
FIG. 2: shows a schematic perspective view of the bottom side of the spacer mould according to FIG. 1.
Figure 10:
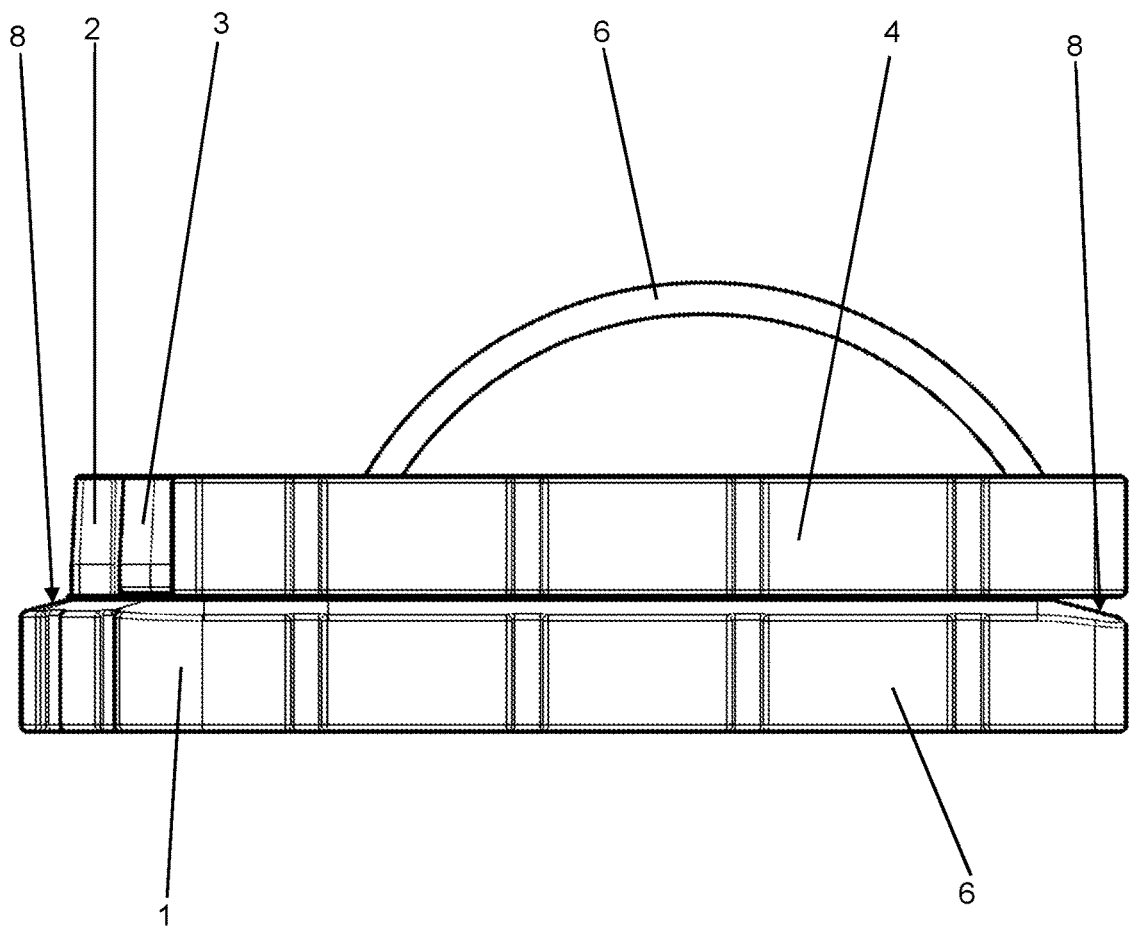
FIG. 10: shows a schematic side view of a spacer mould according to the invention.

FIGS. 1, 2, and 10 show various schematic perspective views of spacer moulds according to the invention. In this context, FIG. 1 shows a perspective view of the top side, FIG. 2 shows a perspective view of the bottom side, and FIG. 10 shows a side view. The spacer mould is assembled from four parts 1, 2, 3, 4, namely a base element 1, a spherical head insert 2, an adapter insert 3, and a punch 4. The base element 1, the spherical head insert 2, the adapter insert 3, and the punch 4 can be assembled without gaps, that means with a perfect fit. In the assembled state, the base element 1, the spherical head insert 2, the adapter insert 3, and the punch 4 form, on their inside, a mould for the spacer to be generated.

The base element 1, the spherical head insert 2, the adapter insert 3, and the punch 4 consist of plastic material, can be produced by means of an injection moulding method, and are intended for single use. A grip 6 is attached to the punch 4 by means of which the punch 4 can be manually pushed onto the base element 1 after the spherical head insert 2 and the adapter insert 3 are inserted into a recess 10 in the base element 1 and after the spherical head insert 2, the adapter insert 3, and a hollow mould 12 (not shown in FIGS. 1 and 2) of the base element 1 have been filled with PMMA bone cement (not shown).

In this context, the punch 4 is being pushed onto a cutting-edge 14 (not shown in FIGS. 1 and 2) at the edge of the hollow mould 12 such that protruding PMMA bone cement is cut off and/or edged off from the PMMA bone cement inside the spacer mould. In order for the cut-off squeezed-out PMMA bone cement to be able to drop off the cutting edge 14, the base element 1 comprises an inclined circumferential surface 8 that drops off from the edge of the hollow mould 12 and from the edge of the recess 10. Since the base element 1 can be set up on a planar surface, such as a table, by its bottom side (shown in FIG. 2), the inclination of the inclined surface 8 leads to the PMMA bone cement being able to flow off or slide off said surface 8 due to the effect of gravity.

Figure 3:
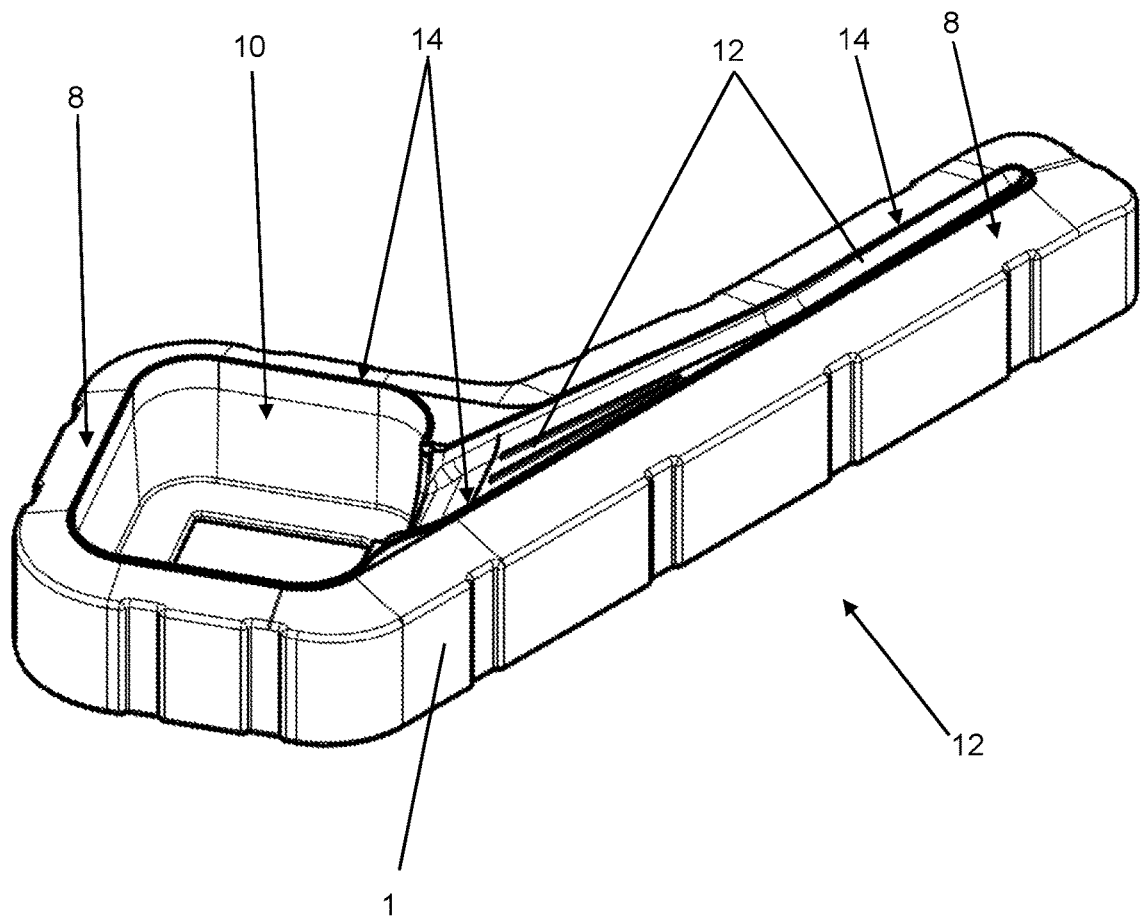
FIG. 3: shows a schematic perspective view of a base element of the spacer mould shown in FIGS. 1 and 2.

FIG. 3 shows a schematic perspective view of the base element 1 of the spacer mould. The hollow mould 12 can be seen in the base element 1 and represents a negative image of the femoral stem 54 of the hip spacer to be generated (see FIG. 9). For this purpose, the hollow mould 12 is being filled with an excess of PMMA bone cement after the spherical head insert 2 and the adapter insert 3 have been inserted into the recessed 10 and before the punch 4 is being pushed on. The edge of the hollow mould 12 and of the recesses 10 on the top side of the base element 1 is bounded by the circumferential cutting edges 14. The cutting edges 14 on the recess 10 are not necessary, since no PMMA bone cement needs to be severed at this site. Prior to filling the hollow mould 12 with an excess of PMMA bone cement, a steel core (or a core made of a different material) for mechanical stabilisation of the hip spacer to be generated is placed in the hollow mould 12.

Figure 4:
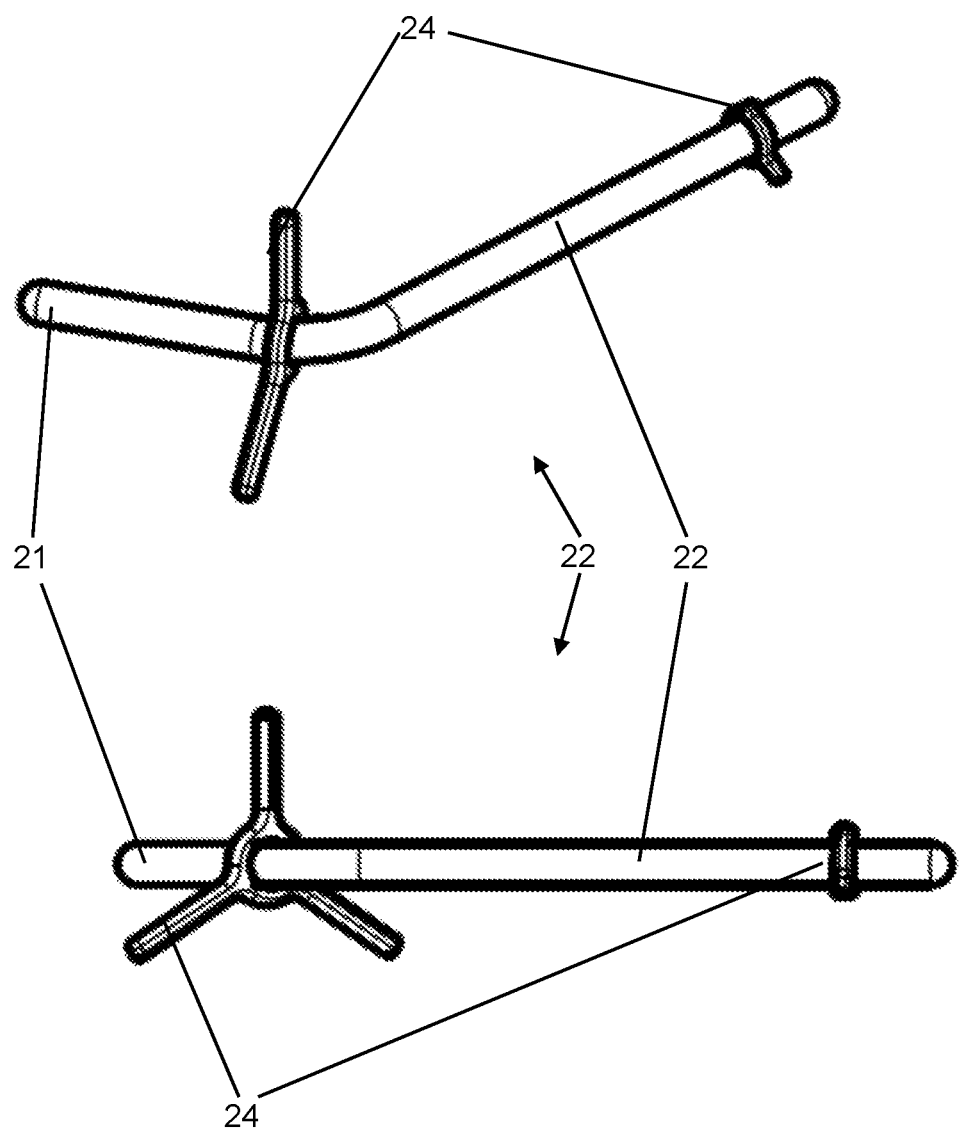
FIG. 4: shows two schematic perspective views of a steel core for producing a hip spacer.

FIG. 4 shows two schematic perspective views of said steel core 20. The steel core 20 comprises a proximal head 21 and a distal stem 22. The head 21 is angled with respect to the stem 22 and firmly connected to same. The steel core 20 is used for producing and/or reinforcing the hip spacer to be produced. Two star-shaped distance pieces 24 made of PMMA are provided in the area of the kink and in the area of the distal end of the stem 22 of the core 20 and enable exact positioning of the steel core 20 in the spacer mould. For this purpose, the three arms each of the distance pieces 24 are supported against the internal walls of the spacer mould, which are formed, inter alia, by the hollow mould 12.

Figure 5:
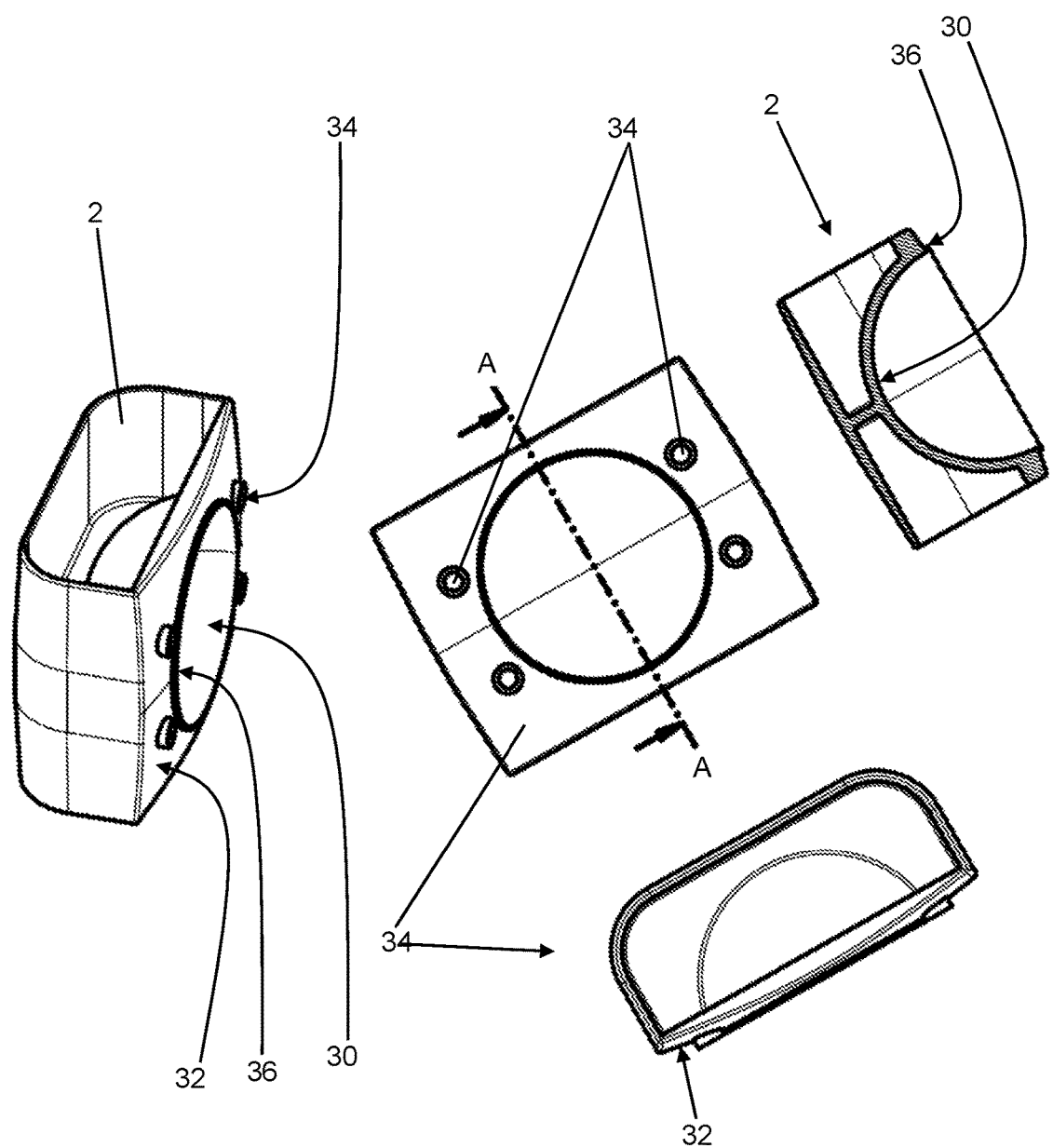
FIG. 5: shows a schematic perspective view (left), a top view (middle), a sectioned view (top right), and another sectioned view (bottom right) of a semi-spherical insert of the spacer mould shown in FIGS. 1 and 2.

FIG. 5 shows a schematic perspective view (FIG. 5 left), a top view (FIG. 5 middle), a view sectioned along the plane A-A with respect to the view shown in the middle of FIG. 5 (FIG. 5 top right), and another view sectioned perpendicular to the plane A-A (FIG. 5 bottom right) of the semi-spherical insert 2 of the spacer mould shown in FIGS. 1, 2, and 10. The semi-spherical insert 2 comprises a semi-spherical femoral head mould 30 that is to be filled with PMMA bone cement and forms a part of the inner spacer mould. The sliding surface of the femoral head 52 of the hip joint spacer is generated by means of said femoral head mould 30 (see FIG. 9). For this purpose, the femoral head mould 30 is provided to be smooth and has no projections. The surface 32 of the semi-spherical insert 2 adjacent to the femoral head mould 30 is provided inclined analogous to the base element 1, such that emerging PMMA bone cement can drop off and/or can become detached into the gap between the semi-spherical insert 2 and the adapter insert 3. Four depressions 34 are provided in said inclined surface 32 as fastening elements 34. Said depressions 34 are to be engaged by pins 46 of the adapter insert 3 (see FIG. 8) in order to connect the semi-spherical insert 2 and the adapter insert 3 to each other in correct position. The invention can provide the depressions 34 to have an unambiguous shape and/or positioning such that they can be connected to the pins 46 of the adapter insert 3 only in a single and unambiguous way in order to exclude faulty operation.

The femoral head mould 30 is bounded by a cutting-edge 36 by means of which the excess of PMMA bone cement is severed when the PMMA bone cement-filled semi-spherical insert 2 and the also PMMA bone cement-filled adapter insert 3 are assembled.

Figure 6:
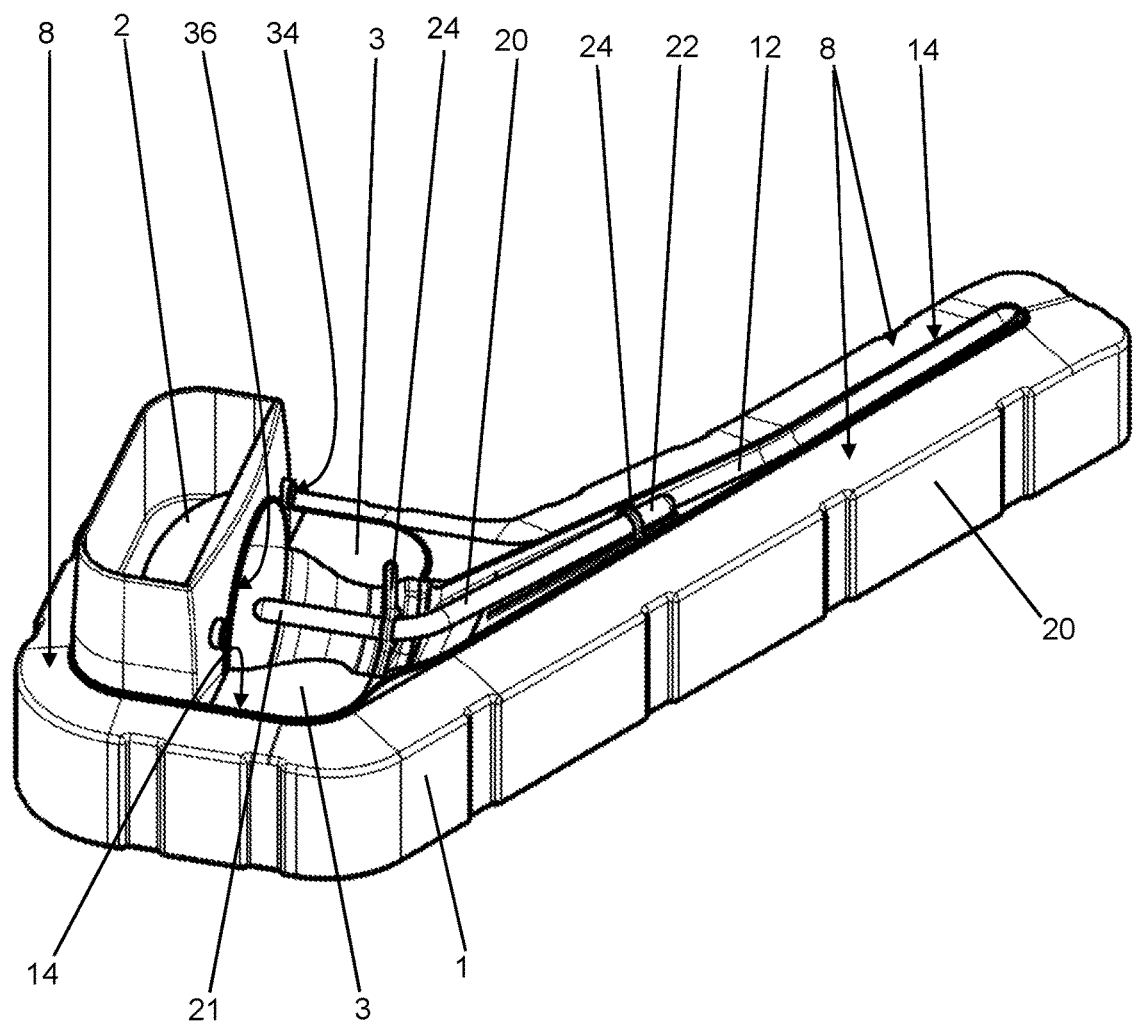
Figure 8:
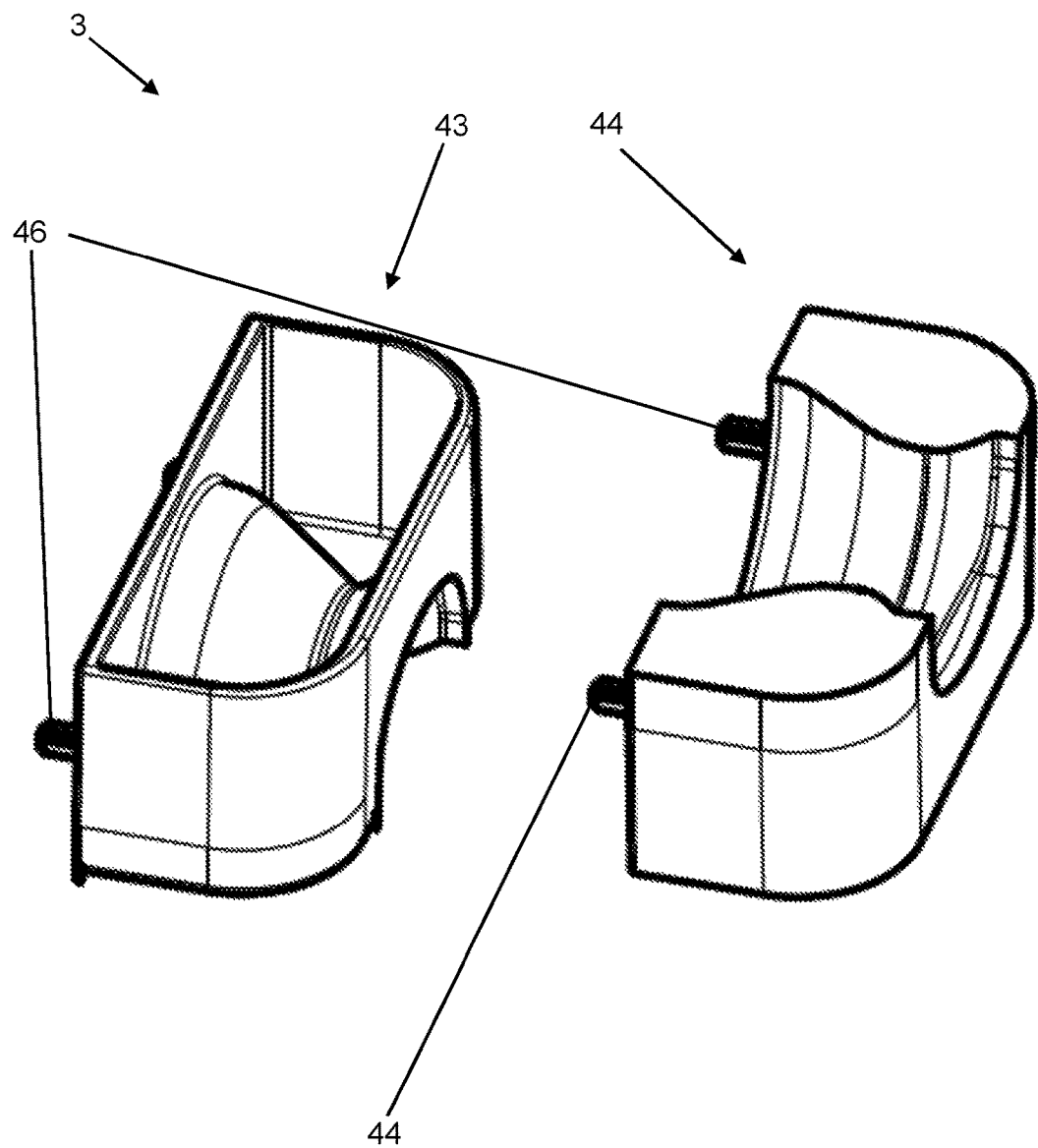
FIG. 8: shows a schematic perspective view of two parts of an adapter insert of the spacer mould shown in FIGS. 1 and 2.

FIG. 6 shows a schematic perspective view of the base element 1 according to FIG. 3, in which the semi-spherical insert 2 according to FIG. 5 and a lower part 44 of an adapter insert 3 according to FIG. 8 are inserted and a steel core 20 according to FIG. 4 is placed in the hollow mould 12 of the base element 1. Accordingly, it is evident from FIG. 6 how the steel core 20 is positioned in the hollow mould 12 and in the hollow body of the adapter insert 3 by means of the distance pieces 24. The status shown in FIG. 6 is not being realised during the production of the hip spacer, since the core 20 is plugged into the adapter insert 3 only after the semi-spherical insert 2 and the adapter insert 3 are filled with PMMA bone cement. Moreover, PMMA bone cement may already have been filled into the hollow mould 12 before the insertion and/or positioning of the core 20 in the hollow mould 12 of the base element 1, whereby it is preferred to keep filling more PMMA bone cement into the core 20 and thus into the hollow mould 12 after the insertion of the core 20, such that the core 20 becomes enveloped by PMMA bone cement.

The lower part 44 of the adapter insert 3 is connected to the semi-spherical insert 2 by pins 46 (not shown in FIG. 6) of the adapter insert 3 being plugged into the depressions 34 of the semi-spherical insert 2. The recess 10 has an inner circumference that is somewhat smaller than the outer circumference of the semi-spherical insert 2 assembled with the adapter insert 3. Simultaneously, the plastic material from which the base element 1 is fabricated is at least somewhat elastic such that the semi-spherical insert 2 assembled with the adapter insert 3 can be plugged into the recess 10. The recess 10 then keeps the semi-spherical insert 2 and the adapter insert 3 together in a press-fit. In this context, the adapter insert 3 is being pressed onto the cutting edge 36 of the semi-spherical insert 2. Protruding PMMA bone cement can thus be severed to be largely free of burrs.

Figure 7:
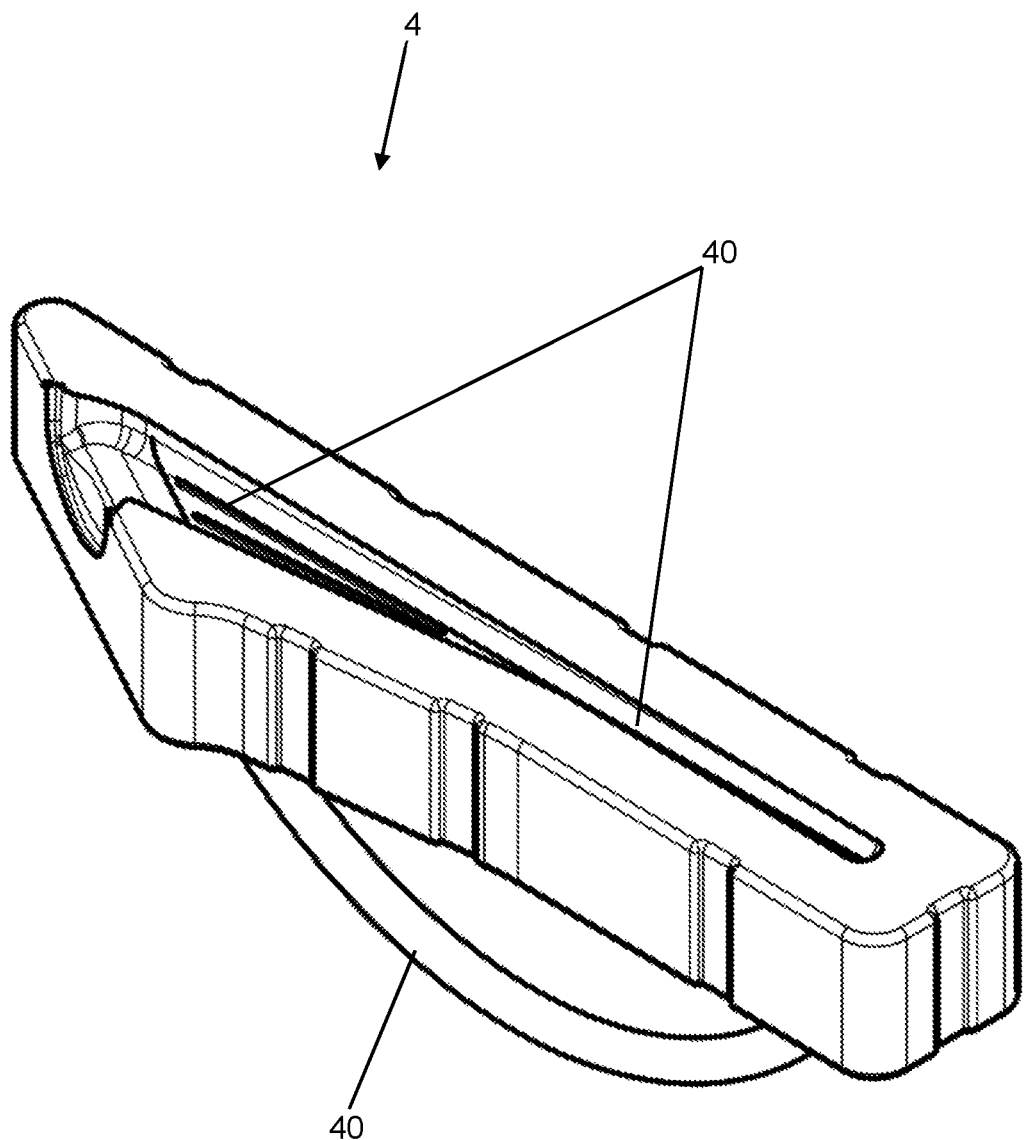
FIG. 7: shows a schematic perspective view of a punch of the spacer mould shown in FIGS. 1 and 2.

FIG. 7 shows a schematic perspective view of a punch 4 of the spacer mould shown in FIGS. 1 and 2. A punch hollow mould 40 is provided in the punch 4 and forms a negative image of the remaining femoral stem 54 of the hip spacer to be generated that is not yet defined through the hollow mould 12 or the hollow body of the adapter insert 3. Applying the punch 4 causes the edge of the punch hollow mould 40 to be pressed onto the cutting edge 14 of the base element 1. In the process, PMMA bone cement emerging from the spacer form is severed and/or cut off without any burrs remaining at the connection. The base element 1 and the punch 4 can comprise guide elements (not shown) that ensure that the punch 4 can be pushed onto the base element 1 in just one orientation and/or positioning.

The punch hollow mould 40 can have multiple through-going bore holes (not shown) provided in it through which the air can escape from the spacer mould when the punch 4 is being applied. Tips arise on the generated stem of the hip spacer in this place and have to be removed, i.e. for example have to be sanded down, after the hip spacer is cured and taken out of the spacer mould.

The invention can provide for various inserts (not shown) for the punch hollow mould 40 and the hollow mould 12 of the base element 1 to be present that can be placed into the punch hollow mould 40 and/or the hollow mould 12 of the base element 1 in order to be able to produce hip spacers with differently-sized or differently-shaped femoral stems. In like manner, various semi-spherically inserts 2 and various adapter inserts 3 can be provided and used to be able to vary the head of the hip spacer to be generated (in particular its diameter, but also its inclination with respect to the femoral stem). Different matching steel cores 20 and matching distance pieces 24 can be provided for all these variants. For this purpose, the distance pieces 24 can initially be present separate from the steel cores 20 and the individually matching distance pieces 24 made of PMMA can be pushed onto the steel cores 20 only right before insertion.

FIG. 8 shows a schematic perspective view of two parts 43, 44 of an adapter insert 3 of the spacer mould shown in FIGS. 1 and 2. The lower part 44 of the adapter insert 3 is inserted into the recess 10 of the base element 1 in the arrangement according to FIG. 6. Alternatively to the embodiment shown, the upper part 43 and the lower part 44 of the adapter insert 3 can be connected to each other by means of cutting edges (not shown) on the edge of the hollow body formed on the inside of the adapter insert 3 (when the two parts 43, 44 are assembled). However, the bur at this site is less disturbing than at other sites of the hip spacer to be generated.

Two pins 46 each are arranged as fastening elements both on the upper part 43 and on the lower part 44 of the adapter insert 3, i.e. on the opening and/or on the connecting surface to the semi-spherical insert 2, whereby the pins 46 can be plugged into the depressions 34 of the semi-spherical insert 2 in order to connect the semi-spherical insert 2 to the adapter insert 3.

In the assembled state, the base element 1, the spherical head insert 2, the adapter insert 3, and the punch 4 form, on their inside, a mould for the spacer to be generated, i.e. they form the spacer mould according to the invention.

A method according to the invention can be implemented with the spacer mould according to the invention, for example as follows:

A semi-spheric insert 2 and an adapter insert 3 matching the treatment situation are selected. The femoral head mould 30 of the semi-spherical insert 2 is filled with an excess of PMMA bone cement. The two parts 43, 44 of the adapter insert 3 are being connected to the semi-spherical insert 2 by means of the fastening means 34, 46. Subsequently, the hollow body of the adapter insert 3 is also being filled with PMMA bone cement through the remaining free opening. Alternatively, the hollow body of the adapter insert 3 can also be filled with PMMA bone cement before or while it is being assembled with the semi-spherical insert 2. Due to the large free cross-sections, the semi-spherical insert 2 and the adapter insert 3 are convenient to fill with the PMMA bone cement. This can be done either with a spatula or with a bone cement applicator (not shown). It is feasible to fill a highly viscous bone cement into the inserts 2, 3.

Subsequently, the semi-spherical insert 2 and the adapter insert 3, attached to each other and filled with PMMA bone cement, are plugged into the recess 10 of the base element 1. Since the recess 10 has a somewhat smaller inner circumference than the outer circumference of the inserts 2, 3 attached to each other, the semi-spherical insert 2 and the adapter insert 3 are pressed onto each other and the cutting edge 36 severs emerging excess PMMA bone cement along the connection of the femoral head mould 30 to the hollow body of the adapter insert 3. Due to the presence of the inclined surface 32 and of the gap, the severed PMMA bone cement can move away and/or slide off from the cutting site. Provided as the negative image of a part of the femoral stem 54 of the hip spacer to be generated (see FIG. 9), the hollow mould 12 of the base element 1, in the inserted state, touches against the remaining free opening of the hollow body of the inserted adapter insert 3.

Inserts for the hollow mould 12 and for the punch hollow mould 40 that match the treatment scenario are being selected and placed into the hollow mould 12 and/or the punch hollow mould 40. This results in a hollow mould 12 modified by the inserts and a modified punch hollow mould 40. Alternatively, the hollow mould 12 and the punch hollow mould 40 can just as well be used in their original shape. Likewise, according to the invention, various space elements 1 and punches 4 with different hollow moulds 12 and/or punch hollow moulds 40 can be kept on stock to allow the ones matching the treatment scenario to be selected.

Subsequently, a head 21 of a core 20 for mechanical stabilisation of the hip spacer is plugged into the PMMA bone cement present in the hollow body of the adapter insert 3 connected (adapter insert 3) to the semi-spherical insert 2, such that a fin 22 of the core 20 is arranged in the hollow mould 12 of the base element 1. Some PMMA bone cement may already have been filled into the hollow mould 12 of the base element 1 at an earlier time. The hollow mould 12 of the base element 1 is being filled with an excess of PMMA bone cement such that the core 20 is enveloped by PMMA bone cement. Distance pieces 24 made of PMMA are used to position the core 20 in the hollow mould 12 and in the hollow body of the adapter insert 3.

Subsequently, the punch 4 with the punch hollow mould 40, possibly modified by an insert, as a negative image of the remaining part of the femoral stem 54 of the hip spacer to be generated (see FIG. 9) is being pushed onto the fluid PMMA bone cement in the hollow mould 12. By this means, the femoral head mould 30, the hollow body of the adapter insert 3, the hollow mould 12 of the base element 1, and the punch hollow mould 40 of the punch 4 define the shape of the hip spacer to be generated. Applying the punch 4, excess PMMA bone cement is severed by the cutting edges 14 at the connection between the hollow mould 12 of the base element 1 and the punch hollow mould 40. Due to the presence of the inclined surface 8 of the base element 1, the severed PMMA bone cement can move away and/or slide off from the cutting site.

Subsequently, after the PMMA bone cement has cured in the spacer mould formed by the base element 1, the semi-spherical insert 2, the adapter insert 3, and the punch 4, the finished hip spacer is taken out of the spacer mould. Burrs and tips that may still be present (which might be generated by the ventilation openings in the punch hollow mould 40) are removed by grinding. The finished hip spacer can then be used for treatment.

Figure 9:
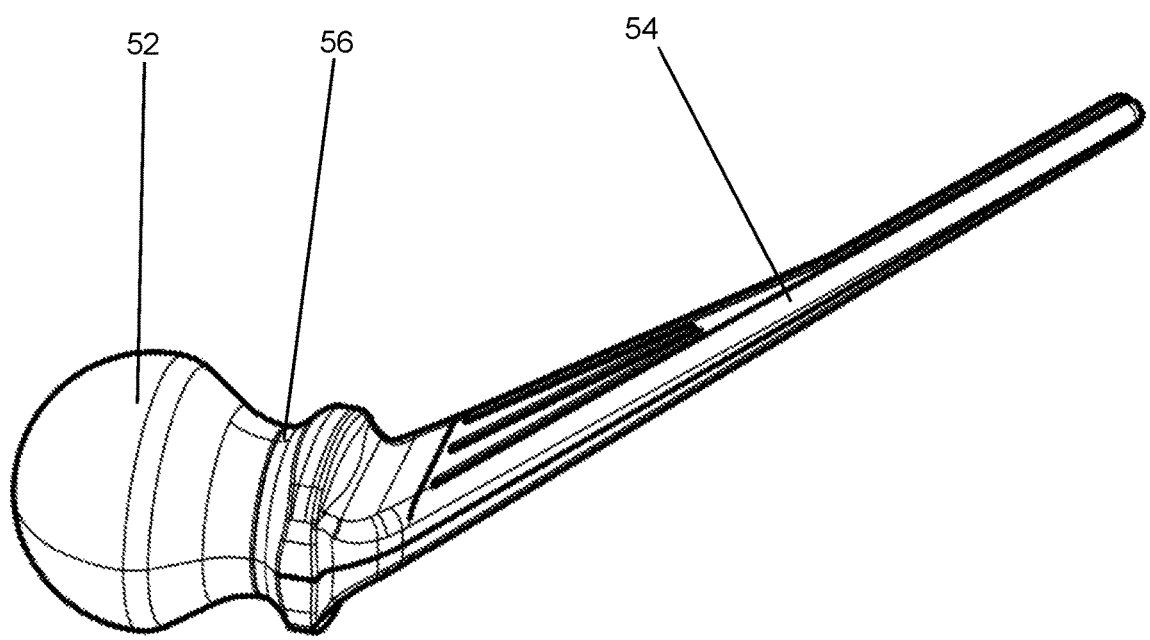
FIG. 9: shows a schematic perspective view of a hip spacer produced with a method according to the invention with a spacer mould according to FIGS. 1 and 2.

FIG. 9 shows a schematic perspective view of said hip spacer that was produced with a method according to the invention with a spacer mould according to FIGS. 1 and 2. The hip spacer comprises a head 52, a femoral stem 54 or stem 54, and a neck 56. The neck 56 connects the stem 54 to the head 52 of the hip spacer. The proximal surface of the head 52 forms the sliding surface of the hip joint and was formed burr-free by the semi-spherical insert 2. The neck 56 and the adjacent parts of the head 52 and of the stem 54 are formed by the hollow body in the adapter insert 3. The remaining stem 54 is formed by the hollow mould 12 in the base element 1 and by the punch hollow mould 40 in the punch 4.

FIG. 10 shows a schematic side view of a spacer mould according to the invention. This view shows the inclination of the downward inclined surface 8 next to the edge of the hollow mould 12 and next to the recess 10 particularly well.

The features of the invention disclosed in the preceding description and in the claims, figures, and exemplary embodiments, can be essential for the implementation of the various embodiments of the invention both alone and in any combination.

LIST OF REFERENCE NUMBERS

1 Base element
2 Semi-spherical insert
3 Adapter insert
4 Punch
6 Handle
8 Inclined surface
10 Recess
12 Hollow mould
14 Cutting edge
20 Steel core
21 Head
22 Fin
24 Distance piece
30 Femoral head mould
32 Inclined surface
34 Depression/fastening element
36 Cutting edge
40 Punch hollow mould
43 Upper part of the adapter insert
44 Lower part of the adapter insert
46 Pin/fastening element
52 Head of the hip spacer
54 Femoral stem of the hip spacer
56 Neck of the hip spacer

The invention claimed is:

1. A spacer mould for producing a hip spacer, the spacer mould comprising:
a base element having a height defined between a top side and a bottom side, wherein a hollow mould is provided on the top side of the base element as a negative image of one side of a femoral stem of the hip spacer to be generated, wherein a recess is provided on the top side of the base element, arranged on an end of the hollow mould in the base element and connected to the hollow mould, wherein the top side of the base element comprises an inclined surface, adjacent to the hollow mound and the recess, that slopes upwardly from a perimeter of the top side to a perimeter of the hollow mould and a perimeter of the recess;
a semi-spherical insert comprising a femoral head mould as a negative image of one side of a femoral head of the hip spacer to be generated, wherein the semi-spherical insert is arrangeable in the recess of the base element at a side of the recess that is opposite to the hollow mould, such that the femoral head mould is aligned in a direction towards the hollow mould;
an adapter insert designed as a hollow body that is open on two sides and that is arrangeable in the recess of the base element between the semi-spherical insert and the hollow mould such that the recess exerts a pressure onto the adapter insert and the semi-spherical insert when the adapter insert and the semi-spherical insert are inserted into the recess, wherein the hollow body of the adapter insert connects the femoral head mould of the semi-spherical insert to the hollow mould in the base element;
a punch comprising a punch hollow mould in a form of the negative image of another side of the femoral stem and that is at least one of arrangeable and pressable onto a top side of the base element;
a first cutting edge bounding a first connection of the hollow mould of the base element to the punch hollow mould of the punch is arranged on at least one of an edge of the hollow mould of the base element and an edge of the punch hollow mould of the punch; and
a second cutting edge bounding a second connection of the femoral head mould to the opening of the hollow body of the adapter insert is arranged on at least one of an edge of the femoral head mould and an edge of said opening of the hollow body of the adapter insert to the femoral head mould.

2. The spacer mould according to claim 1, wherein the femoral head mould of the semi-spherical insert comprises a circumferential edge and the semi-spherical insert has an inclined surface around the circumferential edge of the femoral head mould that slopes downwardly from the circumferential edge to an outer perimeter of the inclined surface.

3. The spacer mould according to claim 1, wherein at least one of: i) the first cutting edge bounds the hollow mould, in its entirety, in the base element, ii) the second cutting edge bounds the femoral head mould, in its entirety, in the semi-spherical insert, and iii) the entire hollow body of the adapter insert, in the connection to the femoral head mould, is bounded by at least one cutting edge of the first and second cutting edges.

4. The spacer mould according to claim 1, wherein the base element comprises, on the bottom side, a planar support surface or a pedestal for set-up of the spacer mould on a planar support.

5. The spacer mould according to claim 1, wherein the adapter insert is a two-part adapter insert or a multi-part adapter insert, wherein parts of the adapter insert are attachable to each other or placeable against each other, wherein the first and second cutting edges are provided on the parts of the adapter insert, wherein the first and second cutting edges are arranged on the edges of moulds forming the hollow body that form the connections of the hollow body in the adapter insert.

6. The spacer mould according to claim 1, wherein the base element is fabricated from plastic material that is elastic such that the semi-spherical insert and the adapter insert are insertable into the recess of the base element.

7. The spacer mould according to claim 1, wherein the recess of the base element has a circumference that is smaller than a circumference of the semi-spherical insert with the adapter insert contacting against the semi-spherical insert.

8. The spacer mould according to claim 1, wherein the semi-spherical insert is provided as a single part.

9. The spacer mould according to claim 1, wherein the width of the semi-spherical insert surrounding the edge of the femoral head mould is between 5 mm and 45 mm.

10. The spacer mould according to claim 1, wherein ventilation openings are provided in the punch or through-going ventilation openings are provided in the punch hollow mould.

11. The spacer mould according to claim 1, wherein the spacer mould comprises no filling openings for adding PMMA bone cement.

12. The spacer mould according to claim 1, wherein the spacer mould comprises at least one insert for at least one of the hollow mould and the punch hollow mould that is insertable into at least one of the hollow mould and the punch hollow mould such that at least one of a size and a shape of the femoral stem of the hip spacer to be generated is varied by means of the at least one insert.

13. A spacer mould for producing a hip spacer, the spacer mould comprising:
- a base element, in which a hollow mould is provided as a negative image of one side of a femoral stem of the hip spacer to be generated, wherein a recess is arranged on an end of the hollow mould in the base element and is connected to the hollow mould;
- a semi-spherical insert comprising a femoral head mould as a negative image of one side of a femoral head of the hip spacer to be generated, wherein the semi-spherical insert is arrangeable in the recess of the base element at a side of the recess that is opposite to the hollow mould, such that the femoral head mould is aligned in a direction towards the hollow mould;
- an adapter insert designed as a hollow body that is open on two sides and that is arrangeable in the recess of the base element between the semi-spherical insert and the hollow mould such that the recess exerts a pressure onto the adapter insert and the semi-spherical insert when the adapter insert and the semi-spherical insert are inserted into the recess, wherein the hollow body of the adapter insert connects the femoral head mould of the semi-spherical insert to the hollow mould in the base element;
- a punch that comprises a punch hollow mould in a form of the negative image of another side of the femoral stem and that is at least one of arrangeable and pressable onto a top side of the base element;
- a first cutting edge bounding a first connection of the hollow mould of the base element to the punch hollow mould of the punch is arranged on at least one of an edge of the hollow mould of the base element and an edge of the punch hollow mould of the punch; and
- a second cutting edge bounding a second connection of the femoral head mould to the opening of the hollow body of the adapter insert is arranged on at least one of an edge of the femoral head mould and an edge of said opening of the hollow body of the adapter insert to the femoral head mould,
- wherein the spacer mould comprises no filling openings for adding PMMA bone cement.

* * * * *